United States Patent [19]
Herrmann et al.

[11] Patent Number: 5,880,302
[45] Date of Patent: Mar. 9, 1999

[54] ORGANOMETALLIC COMPOUND

[75] Inventors: Hans-Friedrich Herrmann, Dornheim; Frank Küber, Oberursel; Wolfgang Anton Herrmann, Freising; Markus Morawietz, Hanau, all of Germany

[73] Assignee: Targor GmbH, Germany

[21] Appl. No.: 942,076

[22] Filed: Oct. 1, 1997

Related U.S. Application Data

[63] Continuation of Ser. No. 646,852, May 8, 1996, abandoned.

[30] Foreign Application Priority Data

May 8, 1995 [DE] Germany ............... 195 16 803.8

[51] Int. Cl.$^6$ .............. C07F 17/00; C07F 7/00; C08F 4/642
[52] U.S. Cl. .............. 556/28; 534/15; 526/127; 526/160; 526/351; 526/943; 502/103; 502/117; 502/153
[58] Field of Search .............. 556/28; 502/103, 502/117, 153; 526/160, 943, 127, 351; 534/15

[56] References Cited

U.S. PATENT DOCUMENTS 5,320,996  6/1994  Carney et al. ............... 502/113

FOREIGN PATENT DOCUMENTS

| | | |
|---|---|---|
| 0 628 565 | 12/1994 | European Pat. Off. . |
| 0 629 632 | 12/1994 | European Pat. Off. . |
| 0 645 401 | 3/1995 | European Pat. Off. . |
| 0 653 433 | 5/1995 | European Pat. Off. . |
| 0 659 756 | 6/1995 | European Pat. Off. . |
| 0 659 757 | 6/1995 | European Pat. Off. . |
| 0 682 042 | 11/1995 | European Pat. Off. . |
| 94/11410 | 5/1994 | WIPO . |

OTHER PUBLICATIONS

Herrmann et al., Journal of Organo Metallic Chemistry, "Tin-bridged ansa-metallocenes of zirconium: synthesis and catalytic performance in olefin polymerization", Elscvier Sciences S.A., C.A. 124–203160 pp. 115–117 (1996).

Halterman, Ronald L., "Synthesis and Applications of Chiral cyclopentadienylmetal Complexes" Chem. Rev. 92, pp. 965–994, 1992.

Primary Examiner—Porfirio Nazario-Gonzalez
Attorney, Agent, or Firm—Connolly & Hutz

[57] ABSTRACT

The invention relates to an organometalic compound of the formula I $$\left[ \begin{array}{c} Y \\ Y \end{array} \diagup M \diagdown \begin{array}{c} L \\ L \end{array} \diagdown T \diagdown \begin{array}{c} L \\ L \end{array} \diagdown M \diagdown \begin{array}{c} Y \\ Y \end{array} \right]_K \quad \text{(I)}$$

where M is a metal atom, L are, independently of one another, identical or different π ligands or other electron donors, T is a tin-containing bridge, Y are identical or different and are each a $C_1$–$C_{20}$-hydrocarbon group, an amide group, an alkoxy group or a halogen atom and K=0 or 1.

The organometallic compound is suitable as catalyst component for olefin polymerization.

14 Claims, No Drawings

ORGANOMETALLIC COMPOUND

This application is a continuation of Ser. No. 08/646,852, which was filed May 8, 1996 and is now abandoned.

The present invention relates to an organometallic compound which can advantageously be used as catalyst component, e.g. for the preparation of polyolefins.

Organometallic compounds of the 4th transition group are, in combination with methylaluminoxane (MAO), active catalysts for olefin polymerization. The preparation of polyolefins using soluble metallocene compounds in combination with aluminoxane or other cocatalysts which, owing to their Lewis acidity, can convert the neutral metallocene into a cation and stabilize the latter is known from the literature.

Metallocenes are of great interest not only for the purposes of polymerization or oligomerization of olefins. They can also be used as hydrogenation, epoxidation, isomerization and C-C-coupling catalysts (Chem. Rev. 1992, 92, 965–994).

Bridged metallocenes previously known are those whose bridge comprises carbon, silicon or germanium units.

It is therefore an object of the invention to provide a new organometallic compound which is suitable, in particular, for the preparation of polyolefins.

The present invention accordingly provides an organometallic compound of the formula I $$\left[ \begin{array}{c} Y \diagdown \diagup L \diagdown \diagup L \diagdown \diagup Y \\ M \quad T \quad M \\ Y \diagup \diagdown L \diagup \diagdown L \diagup \diagdown Y \end{array} \right]_K \quad (I)$$

where M is a metal atom, L are, independently of one another, identical or different π ligands or other electron donors, T is a tin-containing bridge, Y are, independently of one another, identical or different $C_1$–$C_{20}$-hydrocarbon groups, amide groups, alkoxy groups or halogen atoms and K=0 or 1.

M are preferably identical and are titanium, zirconium, hafnium, vanadium, niobium, tantalum, scandium, yttrium or a rare earth metal, particular preference being given to titanium, zirconium and hafnium.

L are preferably unsubstituted or substituted cyclopentadienyl groups. Examples of substituted cyclopentadienyl groups are: tetramethylcyclopentadienyl, methylcyclopentadienyl, methyl-tert-butylcyclopentadienyl, tert-butylcyclopentadienyl, isopropylcyclopentadienyl, dimethylcyclopentadienyl, trimethylcyclopentadienyl, trimethylethylcyclopentadienyl, 5-phenylcyclopentadienyl, diphenylcyclopentadienyl, indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4-naphthyl-indenyl, 2-methyl-4-isopropylindenyl, benzoindenyl, 2-methyl-4,5-benzoindenyl, 2-methyl-α-acenaphthindenyl, 2-methyl-4,6-diisopropylindenyl, fluorenyl, 4-methylfluorenyl or 2,7-di-tert-butylfluorenyl. Examples of electron donors are: O, S, $PR^3$ or $NR^3$, where $R^3$ is hydrogen or a $C_1$–$C_{20}$-tert-hydrocarbon radical such as $C_1$–$C_{10}$-alkyl or $C_6$–$C_{14}$-aryl, for example tert-butylamido, cyclohexylamido, 2,6-diisopropylphenylamido, 2,6-di-tert-butylphenylamido or cyclododecylamido.

When K=0, then T is $[R^1{}_2Sn]_n$, where the radicals $R^1$ are identical or different and are each hydrogen or a $C_1$–$C_{30}$-hydrocarbon radical such as $C_1$–$C_{10}$-alkyl or $C_6$–$C_{14}$-aryl, and n is 1, 2, 3 or 4.

When K=0, examples of preferred bridges T are: dimethylstannyl, methylphenylstannyl, diphenylstannyl, tetramethyldistannyl, stannacyclobutyl, stannacyclopentyl, stannacyclohexyl.

When K=1, then T is a tin atom.

Y is preferably a halogen atom such as fluorine, chlorine, bromine or iodine, an amide group such as $NR^2{}_2$ or an $OR^2$ group, where $R^2$ is a $C_1$–$C_{20}$-hydrocarbon group such as $C_1$–$C_{10}$-alkyl or $C_6$–$C_{14}$-aryl.

Examples of preferred substituents Y are: dimethylamide, diethylamide, fluorine, chlorine, bromine, iodine, methoxy, ethoxy, methyl, benzyl.

When K=0, examples of particularly preferred compounds of the formula I are: bis(dimethylamido)[bis(cyclopentadienyl)dimethylstannyl] zirconium, bis(dimethylamido)[(cyclopentadienyl)(indenyl)dimethylstannyl]zirconium, bis(dimethylamido)[(cyclopentadienyl) (fluorenyl)dimethylstannyl]zirconium, bis(dimethylamido)[bis(indenyl)dimethylstannyl]zirconium, bis(dimethylamido)[bis(2-methylindenyl)dimethylstannyl]zirconium, bis(dimethylamido)[bis(2-methyl-4,6-diisopropylindenyl)dimethylstannyl]zirconium, bis(dimethylamido)[bis(2-methyl-4,5-benzoindenyl)dimethylstannyl]zirconium, bis(dimethylamido)[(indenyl)(fluorenyl)dimethylstannyl]zirconium, [(indenyl)(fluorenyl)dimethylstannyl]zirconium dichloride, bis(dimethylamido)[bis(cyclopentadienyl)dimethylstannyl]hafnium, bis(dimethylamido)[(cyclopentadienyl)(indenyl)dimethylstannyl]hafnium, bis(dimethylamido)[(cyclopentadienyl)(tert-butylamido)dimethylstannyl]zirconium, bis(dimethylamido)[(cyclopentadienyl)(fluorenyl)dimethylstannyl]hafnium, bis(dimethylamido)[bis(indenyl)dimethylstannyl]hafnium, bis(dimethylamido)[bis(2-methylindenyl)dimethylstannyl]hafnium, bis(dimethylamido)[bis(2-methyl-4-phenylindenyl)dimethylstannyl]hafnium, bis(dimethylamido)[bis(2-methyl-4,6-diisopropylindenyl)dimethylstannyl]hafnium, bis(dimethylamido)[bis(2-methyl-4,5-benzoindenyl)dimethylstannyl]hafnium, bis(dimethylamido)[(indenyl)(fluorenyl)dimethylstannyl]hafnium, bis(dimethylamido)[bis(cyclopentadienyl)diphenylstannyl]zirconium, bis(dimethylamido)[(cyclopentadienyl)(indenyl)diphenylstannyl]zirconium, bis(dimethylamido)[(cyclopentadienyl)(fluorenyl)diphenylstannyl]zirconium, bis(dimethylamido)[bis(indenyl)diphenylstannyl]zirconium, bis(dimethylamido)[bis(2-methylindenyl)diphenylstannyl]zirconium, bis(dimethylamido)[bis(2-methyl-4-phenylindenyl)diphenylstannyl]zirconium, bis(dimethylamido)[bis(2-methyl-4,6-diisopropylindenyl)diphenylstannyl]zirconium, bis(dimethylamido)[bis(2-methyl-4,5-benzoindenyl)diphenylstannyl]zirconium, bis(dimethylamido)[(indenyl)(fluorenyl)diphenylstannyl]zirconium, bis(dimethylamido)[bis(cyclopentadienyl)diphenylstannyl]hafnium, bis(dimethylamido)[(cyclopentadienyl)(indenyl)diphenylstannyl]hafnium, bis(dimethylamido)[(cyclopentadienyl)(fluorenyl)diphenylstannyl]hafnium, bis(dimethylamido)[bis(indenyl)diphenylstannyl]hafnium, bis(dimethylamido)[bis(2-methylindenyl)diphenylstannyl]hafnium, bis(dimethylamido)[bis(2-methyl-4-phenylindenyl)diphenylstannyl]hafnium, bis(dimethylamido)[bis(2-methyl-4,6-diisopropylindenyl)diphenylstannyl]hafnium, bis(dimethylamido)[bis(2-methyl-4,5-benzoindenyl)diphenylstannyl]hafnium, bis(dimethylamido)[(indenyl)(fluorenyl)diphenylstannyl]hafnium, bis diethylamido)[bis(cyclopentadienyl)dimethylstannyl]zirconium, bis(diethylamido)[(cyclopentadienyl)(indenyl)dimethylstannyl]zirconium, bis(diethylamido)[

(cyclopentadienyl)(fluorenyl)dimethylstannyl]zirconium, bis(diethylamido)[bis(indenyl)dimethylstannyl]zirconium, bis(diethylamido)[bis(2-methylindenyl)dimethylstannyl] zirconium, bis(diethylamido)[bis(2-methyl-4-phenylindenyl)dimethylstannyl]zirconium, bis (diethylamido)[bis(2-methyl-4,6-diisopropylindenyl) dimethylstannyl]zirconium, bis(diethylamido)[(2-methyl-4,5-benzoindenyl)dimethylstannyl]zirconium, bis (diethylamido)[(indenyl)(fluorenyl)dimethylstannyl] zirconium, bis(diethylamido)[bis(cyclopentadienyl) dimethylstannyl]hafnium, bis(diethylamido)[ (cyclopentadienyl)(indenyl)dimethylstannyl]hafnium, bis (diethylamido)[(cyclopentadienyl)(fluorenyl) dimethylstannyl]hafnium, bis(diethylamido)[bis(indenyl) dimethylstannyl]hafnium, bis(diethylamido)[bis(2-methylindenyl)dimethylstannyl]hafnium, bis(diethylamido) [bis(2-methyl-4-phenylindenyl)dimethylstannyl]hafnium, bis(diethylamido)[bis(2-methyl-4,6-diisopropylindenyl) dimethylstannyl]hafnium, bis(diethylamido)[bis(2-methyl-4,5-benzoindenyl)dimethylstannyl]hafnium, bis (diethylamido)[(indenyl)(fluorenyl)dimethylstannyl] hafnium, bis(diethylamido)[bis(cyclopentadienyl) diphenylstannyl]zirconium, bis(diethylamido)[ (cyclopentadienyl)(indenyl)diphenylstannyl]zirconium, bis (diethylamido)[[(cyclopentadienyl)(fluorenyl) diphenylstannyl]zirconium, bis(diethylamido)[bis(indenyl) diphenylstannyl]zirconium, bis(diethylamido)[bis(2-methylindenyl)diphenylstannyl]zirconium, bis (diethylamido)[bis(2-methyl-4-phenylindenyl) diphenylstannyl]zirconium, bis(diethylamido)[bis(2-methyl-4,6-diisopropylindenyl)diphenylstannyl]zirconium, bis(diethylamido)[bis(2-methyl-4,5-benzoindenyl) diphenylstannyl]zirconium, bis(diethylamido)[(indenyl) (fluorenyl)diphenylstannyl]zirconium, bis(diethylamido) [bis(cyclopentadienyl)diphenylstannyl]hafnium, bis (diethylamido)[(cyclopentadienyl)(indenyl) diphenylstannyl]hafnium, bis(diethylamido)[ (cyclopentadienyl)(fluorenyl)diphenylstannyl]hafnium, bis (diethylamido)[bis(indenyl)diphenylstannyl hafnium, bis (diethylamido)[bis(2-methylindenyl)diphenylstannyl] hafnium, bis(diethylamido)[bis(2-methyl-4-phenylindenyl) diphenylstannyl]hafnium, bis(diethylamido)[bis(2-methyl-4,6-diisopropylindenyl)diphenylstannyl]hafnium, bis (diethylamido)[bis(2-methyl-4,5-benzoindenyl) diphenylstannyl]hafnium, bis(diethylamido)[(indenyl) (fluorenyl)diphenylstannyl]hafnium. When K=1, examples of particularly preferred compounds of the formula I are: [tetrakis(cyclopentadienyl)stannyl]bis{[bis(dimethylamido) ]zirconium}, [bis(cyclopentadienyl)bis(indenyl)stannyl] bis{[bis(dimethylamido)]zirconium}, [bis (cyclopentadienyl)bis(fluorenyl)stannyl]bis{[bis (dimethylamido)]zirconium}, [tetrakis(indenyl)stannyl]bis{ [bis(dimethylamido)]zirconium}, [tetrakis(2-methylindenyl)stannyl]bis{[bis(dimethylamido)] zirconium}, [bis(indenyl)bis(2-methylindenyl)stannyl]bis{ [bis(dimethylamido)]zirconium}, [tetrakis(2-methyl-4-phenylindenyl)stannyl]bis{[bis(dimethylamido)] zirconium}, [tetrakis(2-methyl-4,5-benzoindenyl)stannyl] bis{[bis(dimethylamido)]zirconium}, [tetrakis (cyclopentadienyl)stannyl]bis{[bis(dimethylamido)] hafnium}, [bis(cyclopentadienyl)bis(indenyl)stannyl]bis{ [bis(dimethylamido)]hafnium}, [bis(cyclopentadienyl)bis (fluorenyl)stannyl]bis{[bis(dimethylamido)]hafnium}, [tetrakis(indenyl)stannyl]bis{[bis(dimethylamido)] hafnium}, [tetrakis(2-methylindenyl)stannyl]bis{[bis (dimethylamido)]hafnium}, [bis(indenyl)bis(2-methylindenyl)stannyl]bis{[bis(dimethylamido)hafnium}, [tetrakis(2-methyl-4-phenylindenyl)stannyl]bis{[bis (dimethylamido)]hafnium}, [tetrakis(2-methyl-4,5-benzoindenyl)stannyl]bis{[bis(dimethylamido)]hafnium}, [tetrakis(cyclopentadienyl)stannyl]bis{[bis(diethylamido)] zirconium}, [bis(cyclopentadienyl)bis(indenyl)stannyl]bis{ [bis(diethylamido)]zirconium}, [bis(cyclopentadienyl)bis (fluorenyl)stannyl]bis{[bis(diethylamido)]zirconium}, [tetrakis(indenyl)stannyl]bis{[bis(diethylamido)] zirconium}, [tetrakis(2-methylindenyl)stannyl]bis{[bis (diethylamido)]zirconium}, [bis(indenyl)bis(2-methylindenyl)stannyl]bis{[bis(diethylamido)]zirconium}, [tetrakis(2-methyl-4-phenylindenyl)stannyl]bis{[bis (diethylamido)]zirconium; [tetrakis(2-methyl-4,5-benzoindenyl)stannyl]bis{[bis(diethylamido)]zirconium], [tetrakis(cyclopentadienyl)stannyl]bis{[bis(diethylamido)] hafnium}, [bis(cyclopentadienyl)bis(indenyl)stannyl]bis{ [bis(diethylamido)]hafnium}, [bis(cyclopentadienyl)bis (fluorenyl)stannyl]bis{[bis(diethylamido)]hafnium}, [tetrakis(indenyl)stannyl]bis{[bis(diethylamido)]hafnium}, [tetrakis(2-methylindenyl)stannyl]bis{[bis(diethylamido)] hafnium}, [bis(indenyl)bis(2-methylindenyl)stannyl]bis{ [bis(diethylamido)]hafnium}, [tetrakis(2-methyl-4-phenylindenyl)stannyl]bis{[bis(di20 ethylamido)]hafnium}, [tetrakis(2-methyl-4,5-benzoindenyl)stannyl]bis{[bis (diethylamido)]hafnium}.

The present invention also provides a process for preparing an organometallic compound of the formula 1, where Y is an amide group such as $NR^2_2$, where $R^2$ are, independently of one another, identical or different and are each hydrogen or a $C_1$–$C_{20}$-hydrocarbon radical such as $C_1$–$C_{10}$-alkyl or $C_6$–$C_{14}$-aryl, which comprises reacting a compound of the formula II, where L are identical or different π ligands, T is a tin-containing bridge and K is zero or 1, with a compound of the formula III, where M is a metal atom and $R^2$ are, independently of one another, identical or different and are each hydrogen or a $C_1$–$C_{20}$-hydrocarbon radical such as $C_1$–$C_{10}$-alkyl or $C_6$–$C_{14}$-aryl.

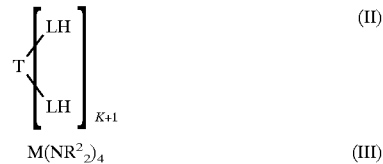

Organometallic compounds of the formula I in which Y is a $C_1$–$C_{20}$-hydrocarbon group, a halogen atom or an alkoxy group can be prepared as described in EP 320 762, which is hereby expressly incorporated by reference.

The reaction is preferably carried out in an aprotic solvent, e.g. toluene or hexane. The temperature can be between −78° and 140° C., preferably from 0° to 110° C. The compound of the formula II is reacted stoichiometrically with the metal amide of the formula III.

The process for preparing the compound of the formula II is known (J. Organomet. Chem. 4 (1965) 313–319). The process for preparing compounds of the formula III is likewise known (J. Chem. Soc. 1960, 3857–3861).

Organometallic compounds of the formula I are, in combination with a cocatalyst, suitable catalysts for the polymerization of olefins to prepare olefin polymers.

The present invention accordingly also provides a process for preparing a polyolefin by polymerization of at least one olefin in the presence of a catalyst, wherein the catalyst comprises at least one organometallic compound of the formula I and at least one cocatalyst. The polymerization can be a homopolymerization or a copolymerization.

Preference is given to homopolymerizing or copolymerizing olefins of the formula $R^a$—CH=CH—$R^b$, where $R^a$ and $R^b$ are identical or different and are each a hydrogen atom or a hydrocarbon radical having from 1 to 20 carbon atoms, in particular from 1 to 10 carbon atoms, or $R^a$ and $R^b$ together with the atoms connecting them form one or more rings. Examples of such olefins are 1-olefins such as ethylene, propylene, 1-butene, 1-pentene, 1-hexene, 4-methyl-1-pentene or 1-octene, styrene, dienes such as 1,3-butadiene or 1,4-hexadiene and cyclic olefins such as norbornene, tetracyclododecene, norbornadiene or vinylnorbornene. In the process of the invention, preference is given to homopolymerizing ethylene or propylene or copolymerizing ethylene with one or more 1-olefins having 3–20 carbon atoms, for example propylene, and/or one or more dienes having 4–20 carbon atoms, for example 1,4-butadiene. Examples of such copolymers are ethylene-propylene copolymers and ethylene-propylene-1,4-hexadiene copolymers.

The polymerization is preferably carried out at a temperature of from −60° to 250° C., particularly preferably from 50° to 200° C. The pressure is preferably from 0.5 to 2000 bar, particularly preferably from 5 to 64 bar.

The polymerization can be carried out in solution, in bulk, in suspension or in the gas phase, continuously or batchwise, in one or more stages. A preferred embodiment is gas-phase polymerization.

The catalyst used in the process of the invention preferably comprises one organometallic compound of the formula I. It is also possible to use mixtures of two or more organometallic compounds of the formula I, or mixtures of organometallic compounds of the formula I with other metallocenes or classical Ziegler-Natta catalysts, e.g. for preparing polyolefins having a broad or multimodal molecular weight distribution.

In the process of the invention, the cocatalyst can in principle be any compound which, owing to its Lewis acidity, can convert the neutral metallocene into a cation and stabilize the latter ("labile coordination"). Furthermore, the cocatalyst or the anion formed therefrom should undergo no further reactions with the metallocene cation formed (EP 427 697). The cocatalyst used is preferably an aluminum compound and/or a boron compound.

The boron compound preferably has the formula $R^3_xNH_{4-x}BR^4_4$, $R^3_xPH_{4-x}BR^4_4$, $R_3CBR^4_4$ or $BR_3$, where x is a number from 1 to 4, preferably 3, the radicals $R^3$ are identical or different, preferably identical, and are $C_1$–$C_{10}$-alkyl or $C_6$–$C_{18}$-aryl, or two radicals $R^3$ together with the atoms connecting them form a ring, and the radicals $R^4$ are identical or different, preferably identical, and are $C_6$–$C_{18}$-aryl which can be substituted by alkyl, haloalkyl or fluorine. In particular, $R^3$ is ethyl, propyl, butyl or phenyl and $R^4$ is phenyl, pentafluorophenyl, 3,5-bistrifluoromethylphenyl, mesityl, xylyl or tolyl (EP 277 003, EP 277 004 and EP 426 638).

The cocatalyst used is preferably an aluminum compound such as aluminoxane and/or an aluminum alkyl.

The cocatalyst used is particularly preferably an aluminoxane, in particular of the formula IVa for the linear type and/or the formula IVb for the cyclic type,

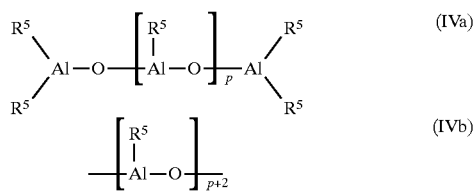

where, in the formulae IVa and IVb, the radicals $R^5$ are identical or different and are each hydrogen or a $C_1$–$C_{20}$-hydrocarbon group such as a $C_1$–$C_{18}$-alkyl group, a $C_6$–$C_{18}$-aryl group or benzyl, and p is an integer from 2 to 50, preferably from 10 to 35.

The radicals $R^5$ are preferably identical and are hydrogen, methyl, isobutyl, phenyl or benzyl, particularly preferably methyl.

If the radicals $R^5$ are different, they are preferably methyl and hydrogen or alternatively methyl and isobutyl, with hydrogen or isobutyl preferably being present in a proportion of from 0.01 to 40% (of the radicals $R^5$).

The methods of preparing the aluminoxanes are known (DE 4 004 477).

The exact spatial structure of the aluminoxanes is not known (J. Am. Chem. Soc. (1993) 115, 4971). For example, it is conceivable that chains and rings are joined to form larger two-dimensional or three-dimensional structures.

Regardless of the method of preparation, all aluminoxane solutions have in common varying contents of unreacted aluminum starting compound which is present in free form or as adduct.

It is possible to preactivate the metallocene compound of the invention prior to use in the polymerization reaction using a cocatalyst, in particular an aluminoxane. This significantly increases the polymerization activity. The preactivation of the metallocene compound is preferably carried out in solution. Here, the metallocene compound is preferably dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total amount of solution. The metallocene can be used in the same concentration, but it is preferably used in an amount of $10^4$–1 mol per mol of aluminoxane. The preactivation time is from 5 minutes to 60 hours, preferably from 5 to 60 minutes. The preactivation is preferably carried out at a temperature of from −78° to 100° C., preferably from 0° to 70° C.

Here, the metallocene compound is preferably used in a concentration, based on the transition metal, of from $10^{-3}$ to $10^{-8}$ mol, preferably from $10^{-4}$ to $10^{-7}$ mol, of transition metal per $dm^3$ of solvent or per $dm^3$ of reactor volume. The aluminoxane is preferably used in a concentration of from $10^{-6}$ to $10^{-1}$ mol, preferably from $10^{-5}$ to $10^{-2}$ mol, per $dm^3$ of solvent or per $dm^3$ of reactor volume. The other cocatalysts mentioned are used in approximately equimolar amounts to the metallocene compound. However, higher concentrations are also possible in principle.

To remove catalyst poisons present in the olefin, purification using an aluminum compound, preferably an aluminum alkyl such as trimethylaluminum or triethylaluminum is advantageous. This purification can be carried out either in the polymerization system itself or the olefin is, prior to addition to the polymerization system, brought into contact with the aluminum compound and subsequently separated off again.

As molecular weight regulator and/or to increase the activity, it is possible to add hydrogen in the process of the invention. This enables low molecular weight polyolefins such as waxes to be obtained.

In the process of the invention, the metallocene compound is preferably reacted with the cocatalyst outside the polymerization reactor in a separate step using a suitable solvent. Application to a support can also be carried out during this step.

In the process of the invention, a prepolymerization can be carried out with the aid of the metallocene compound. For the prepolymerization, the (or one of the) olefin(s) used in the polymerization is preferably employed.

The catalyst used in the process of the invention can be supported. Application to a support enables, for example, the particle morphology of the polyolefin prepared to be controlled. Here, the metallocene compound can be first reacted with the support and subsequently with the cocatalyst. The cocatalyst can also first be supported and subsequently reacted with the metallocene compound. It is also possible to support the reaction product of metallocene compound and the catalyst. Suitable support materials are, for example, silica gels, aluminum oxides, solid aluminoxane or other inorganic support materials such as magnesium chloride. Another suitable support material is a polyolefin powder in finely divided form. The preparation of the supported cocatalyst can be carried out, for example, as described in EP 567 952.

If the polymerization is carried out as a suspension or solution polymerization, an inert solvent customary for the Ziegler low-pressure process is used. For example, the polymerization is carried out in an aliphatic or cycloaliphatic hydrocarbon; examples which may be mentioned of such hydrocarbons are propane, butane, hexane, heptane, isooctane, cyclohexane and methylcyclohexane. A petroleum or hydrogenated diesel oil fraction can also be used. It is also possible to use toluene. Preference is given to carrying out the polymerization in the liquid monomer.

If inert solvents are used, the monomers are metered in in gaseous or liquid form.

The polymerization time can be any desired, since the catalyst system to be used in the process of the invention has only a slight time-dependent decrease in the polymerization activity.

The polymers prepared by the process of the present invention are particularly suitable for producing shaped bodies such as films, plates or large hollow bodies (e.g. tubes).

The following examples illustrate the invention:

All glass apparatus were baked out in vacuo and flushed with argon. All operations were carried out with exclusion of moisture and oxygen in Schlenk vessels. The solvents used were distilled from an Na/K alloy under argon.

Toluene-soluble methylaluminoxane was used for the polymerization examples as a 10% strength by weight toluene solution having a mean degree of oligomerization of n=20 (Witco). According to an aluminum determination, the solution contains 36 mg/Al/ml.

Definitions:
VN=viscosity number
$M_w$=weight average molecular weight (determined by gel permeation chromatography)
$M_w/M_n$=polydispersity 1) Bis(dimethylamido)[bis(cyclopentadienyl) dimethylstannyl zirconium 1:

360 mg (1.29 mmol) of bis(cyclopentadienyl) dimethylstannane and 345 mg (1.29 mmol) of tetrakis (dimethylamido)zirconium are each dissolved in 50 ml of toluene and cooled to −78° C. At this temperature, the dissolved stannyl ligand is added dropwise. On warming to room temperature, the mixture acquires a yellow color. The reaction mixture is stirred for 24 hours at 25° C. (the reaction can be accelerated by gentle warming to about 50° C.). The solvent is removed under reduced pressure and 1 remains as a yellow solid. Yield: 580 mg (1.27 mmol, 99%).

$^1$H-NMR (400 MHz, $C_6D_6$, 25° C.): [ppm] δ=0.28 (s, 6H, $^2J(^{119}Sn, H)$=63.5 Hz, $^2J(^{117}Sn,H)$=60.4 Hz; Sn(C$\underline{H}_3$)$_2$, 2.83 (s, 12H; N(C$\underline{H}_3$)$_2$), 5.75 (t, 1H, $^3J(H,H)$=2.4 Hz, $^4J(^{119/117}Sn,H)$=14.7 Hz; olef. β—C$\underline{H}$), 6.65 (t, 1H, $^3J(H,H)$=2.4 Hz, $^3J(^{119/117}Sn,H)$=11.6 Hz; olef. α—C$\underline{H}$).

2) [Tetrakis(cyclopentadienyl)stannyl]bis{[bis (dimethylamido)]zirconium} 2:

200 mg (0.53 mmol) of tetra(cyclopentadienyl)stannane and 282 g (1.29 mmol) of tetrakis(dimethylamido)zirconium are each dissolved in 15 ml of toluene and cooled to −78° C. At this temperature, the dissolved ligand is added dropwise. On warming to room temperature, the mixture acquires an intense yellow color and begins to become distinctly turbid. The reaction mixture is stirred for 24 hours at 25° C. The solvent is removed under reduced pressure. The yellow residue is washed twice with 10 ml of hexane and 2 is obtained as a yellow powder. Yield: 315 mg (0.43 mmol), 81%).

$^1$H-NMR (400 MHz, $C_6D_6$, 25° C.: [ppm] δ=2.73 (s, 24 H; N(C$\underline{H}_3$)$_2$), 5.92 (t, 1H, $^3J(H,H)$=2.4 Hz, $^4J^{119/117}Sn,H)$=17.7 Hz; olef. β—C$\underline{H}$), 6.62 (t, 1H, $^3J(H,H)$=2.4 Hz, $^3J^{119/117}Sn,H)$=15.9 Hz; olef. α—C$\underline{H}$).

POLYMERIZATION EXAMPLE 1

3.5 mg of the metallocene 1 (9.5, μmol of Zr) were dissolved in 5 ml of 10% strength MAO solution in toluene (total of 6 mmol of Al) and stirred for 1 5 minutes. In parallel thereto, a 1.5 dm$^3$ stirred reactor which has been made inert is charged with 750 ml of diesel oil (boiling point 100°–120° C.) and heated to 70° C. The catalyst solution is metered in and polymerization is carried out for 1 hour at 750 rpm using 7 bar of ethylene. The reactor is subsequently vented, the polymer is filtered from the suspension, washed with acetone and dried for 12 hours in a vacuum drying oven. This gives 35 g of polyethylene, corresponding to 3.68 kg of PE/mmol of Zr, having a VN of 914 ml/g.

POLYMERIZATION EXAMPLE 2

Example 1 was repeated using 2 mg (4.4 μmol of Zr) of the metallocene 1. This gives 30.1 g of PE, corresponding to 6.84 kg of PE/mmol of Zr, having a VN of 240 ml/g.

We claim:
1. An organometallic compound of the formula I

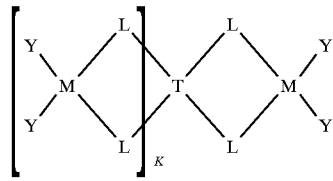

where M are identical or different and are titanium, zirconium, hafnium, vanadium, niobium, tantalum, scandium, yttrium or a rare earth metal, L are, independently of one another, identical or different π ligands or other electron donors, T is a tin-containing bridge, Y are identical or different are each a $C_1$–$C_{20}$-hydrocarbon group, an amide group, an alkoxy group or a halogen atom and K=1.

2. An organometallic compound as claimed in claim 1, wherein L are substituted or unsubstituted cyclopentadienyl groups.

3. An organometallic compound as claimed in claim 1, wherein T is a tin atom.

4. A catalyst component comprising at least one organometallic compound as claimed in claim 1 and at least one cocatalyst.

5. A catalyst component as claimed in claim 4, additionally containing a support.

6. The compound as claimed in claim 1, wherein M is titanium, zirconium, hafnium, vanadium, niobium or a rare earth metal.

7. The compound as claimed in claim 2, wherein M is titanium, zirconium or hafnium.

8. The compound as claimed in claim 1, wherein the compound is selected of the group consisting of bis(dimethylamido)[bis(cyclopentadienyl)dimethylstannyl]zirconium, bis(dimethylamido)[(cyclopentadienyl)(indenyl)dimethylstannyl]zirconium, bis(dimethylamido)[(cyclopentadienyl)(fluorenyl)dimethylstannyl]zirconium, bis(dimethylamido)[bis(indenyl)dimethylstannyl]zirconium, bis(dimethylamido)[bis(2-methylindenyl)dimethylstannyl]zirconium, bis(dimethylamido)[bis(2-methyl-4,6-diisopropylindenyl)dimethylstannyl]zirconium, bis(dimethylamido)[bis(2-methyl-4,5-benzoindenyl)dimethylstannyl]zirconium, bis(dimethylamido)[(indenyl)(fluorenyl)dimethylstannyl]zirconium, [(indenyl)(fluorenyl)dimethylstannyl]zirconium dichloride, bis(dimethylamido)[bis(cyclopentadienyl)dimethylstannyl]hafnium, bis(dimethylamido)[(cyclopentadienyl)(indenyl)dimethylstannyl]hafnium, bis(dimethylamido)[(cyclopentadienyl)(tert-butylamido)dimethylstannyl]zirconium, bis(dimethylamido)[(cyclopentadienyl)(fluorenyl)dimethylstannyl]hafnium, bis(dimethylamido)[bis(indenyl)dimethylstannyl]hafnium, bis(dimethylamido)[bis(2-methylindenyl)dimethylstannyl]hafnium, bis(dimethylamido)[bis(2-methyl-4-phenylindenyl)dimethylstannyl]hafnium, bis(dimethylamido)[bis(2-methyl-4,6-diisopropylindenyl)dimethylstannyl]hafnium, bis(dimethylamido)[bis(2-methyl-4,5-benzoindenyl)dimethylstannyl]hafnium, bis(dimethylamido)[(indenyl)(fluorenyl)dimethylstannyl]hafnium, bis(dimethylamido)[bis(cyclopentadienyl)diphenylstannyl]zirconium, bis(dimethylamido)[(cyclopentadienyl)(indenyl)diphenylstannyl]zirconium, bis(dimethylamido)[(cyclopentadienyl)(fluorenyl)diphenylstannyl]zirconium, bis(dimethylamido)[bis(indenyl)diphenylstannyl]zirconium, bis(dimethylamido)[bis(2-methylindenyl)diphenylstannyl]zirconium, bis(dimethylamido)[bis(2-methyl-4-phenylindenyl)diphenylstannyl]zirconium, bis(dimethylamido)[bis(2-methyl-4,6-diisopropylindenyl)diphenylstannyl]zirconium, bis(dimethylamido)[bis(2-methyl-4,5-benzoindenyl)diphenylstannyl]zirconium, bis(dimethylamido)[(indenyl)(fluorenyl)diphenylstannyl]zirconium, bis(dimethylamido)[bis(cyclopentadienyl)diphenylstannyl]hafnium, bis(dimethylamido)[(cyclopentadienyl)(indenyl)diphenylstannyl]hafnium, bis(dimethylamido)[(cyclopentadienyl)(fluorenyl)diphenylstannyl]hafnium, bis(dimethylamido)[bis(indenyl)diphenylstannyl]hafnium, bis(dimethylamido)[bis(2-methylindenyl)diphenylstannyl]hafnium, bis(diethylamido)[bis(2-methyl-4-phenylindenyl)diphenylstannyl]hafnium, bis(diethylamido)[bis(2-methyl-4,6-diisopropylindenyl)diphenylstannyl]hafnium, bis(diethylamido)[bis(2-methyl-4,5-benzoindenyl)diphenylstannyl]hafnium, bis(diethylamido)[(indenyl)(fluorenyl)diphenylstannyl]hafnium, bis(diethylamido)[bis(cyclopentadienyl)dimethylstannyl]zirconium, bis(diethylamido)[(cyclopentadienyl)(indenyl)dimethylstannyl]zirconium, bis(diethylamido)[(cyclopentadienyl)(fluorenyl)dimethylstannyl]zirconium, bis(diethylamido)[bis(indenyl)dimethylstannyl]zirconium, bis(diethylamido)[bis(2-methylindenyl)dimethylstannyl]zirconium, bis(diethylamido)[bis (2-methyl-4-phenylindenyl)dimethylstannyl]zirconium, bis(diethylamido)[bis(2-methyl-4,6-diisopropylindenyl)dimethylstannyl]zirconium, bis(diethylamido)[(2-methyl-4,5-benzoindenyl)dimethylstannyl]zirconium, bis(diethylamido)[(indenyl)(fluorenyl)dimethylstannyl]zirconium, bis(diethylamido)[bis(cyclopentadienyl)dimethylstannyl]hafnium, bis(diethylamido)[(cyclopentadienyl)(indenyl)dimethylstannyl]hafnium, bis(diethylamido)[(cyclopentadienyl)(fluorenyl)dimethylstannyl]hafnium, bis(diethylamido)[bis(indenyl)dimethylstannyl]hafnium, bis(diethylamido)[bis(2-methylindenyl)dimethylstannyl]hafnium, bis(diethylamido)[bis(2-methyl-4-phenylindenyl)dimethylstannyl]hafnium, bis(diethylamido)[bis(2-methyl-4,6-diisopropylindenyl)dimethylstannyl]hafnium, bis(diethylamido)[bis(2-methyl-4,5-benzoindenyl)dimethylstannyl]hafnium, bis(diethylamido)[(indenyl)(fluorenyl)dimethylstannyl]hafnium, bis(diethylamido)[bis(cyclopentadienyl)diphenylstannyl]zirconium, bis(diethylamido)[(cyclopentadienyl)(indenyl)diphenylstannyl]zirconium, bis(diethylamido)[[(cyclopentadienyl)(fluorenyl)diphenylstannyl]zirconium, bis(diethylamido)[bis(indenyl)diphenylstannyl]zirconium, bis(diethylamido)[bis(2-methylindenyl)diphenylstannyl]zirconium, bis(diethylamido)[bis(2-methyl-4-phenylindenyl)diphenylstannyl]zirconium, bis(diethylamido)[bis(2-methyl-4,6-diisopropylindenyl)diphenylstannyl]zirconium, bis(diethylamido)[bis(2-methyl-4,5-benzoindenyl)diphenylstannyl]zirconium, bis(diethylamido)[(indenyl)(fluorenyl)diphenylstannyl]zirconium, bis(diethylamido)[bis(cyclopentadienyl)diphenylstannyl]hafnium, bis(diethylamido)[(cyclopentadienyl)(indenyl)diphenylstannyl]hafnium, bis(diethylamido)[(cyclopentadienyl)(fluorenyl)diphenylstannyl]hafnium, bis(diethylamido)[bis(indenyl)diphenylstannyl]hafnium, bis(diethylamido)[bis(2-methylindenyl)diphenylstannyl]hafnium, bis(diethylamido)[bis(2-methyl-4-phenylindenyl)diphenylstannyl]hafnium, bis(diethylamido)[bis(2-methyl-4,6-diisopropylindenyl)diphenylstannyl]hafnium, bis(diethylamido)[bis(2-methyl-4,5-benzoindenyl)diphenylstannyl]hafnium, bis(diethylamido)[(indenyl)(fluorenyl)diphenylstannyl]hafnium. [tetrakis(cyclopentadienyl)stannyl]bis{[bis(dimethylamido)]zirconium}, [bis(cyclopentadienyl)bis(indenyl)stannyl]bis{(bis(dimethylamido)]zirconium}, [(bis(cyclopentadienyl)bis(fluorenyl)stannyl]bis{[bis(dimethylamido)]zirconium}, [tetrakis(indenyl)stannyl]bis{[bis(dimethylamido)]zirconium}, [tetrakis(2-methylindenyl)stannyl]bis({[bis(dimethylamido)]zirconium}, [bis(indenyl)bis(2-methylindenyl)stannyl]bis{[bis(dimethylamido)]zirconium}, [tetrakis(2-methyl-4-phenylindenyl)stannyl]bis{[bis(dimethylamido)]zirconium}, [tetrakis(2-methyl-4,5-benzoindenyl)stannyl]bis{[bis(dimethylamido)]zirconium}, [tetrakis(cyclopentadienyl)stannyl]bis{[bis(dimethylamido)]hafnium}, [bis(cyclopentadienyl)bis(indenyl)stannyl]bis{[bis(dimethylamido)]hafnium}, [bis(cyclopentadienyl)bis(fluorenyl)stannyl]bis{[bis(dimethylamido)]hafnium}, [tetrakis(indenyl)stannyl]bis{[bis(dimethylamido)]hafnium}, [tetrakis(2-methylindenyl)stannyl]bis{[bis(dimethylamido)]hafnium}, [bis(indenyl)bis(2-methylindenyl)stannyl]bis{]bis(dimethylamido)hafnium}, [tetrakis(2-methyl-4-phenylindenyl)stannyl]bis{[bis(dimethylamido)]hafnium}, [tetrakis(2-methyl-4,5-benzoindenyl)stannyl]bis{[bis(dimethylamido)]hafnium}, [tetrakis(cyclopentadienyl)stannyl]bis{[bis(diethylamido)]zirconium}, [bis(cyclopentadienyl)bis(indenyl)stannyl]bis{[bis(diethylamido)]zirconium}, [bis(cyclopentadienyl)bis (fluorenyl)stannyl]bis{[bis(diethylamido)]zirconium},
[tetrakis(indenyl)stannyl]bis{[bis(diethylamido)]
zirconium}, [tetrakis(2-methylindenyl)stannyl]bis{[bis
(diethylamido)]zirconium}, [bis(indenyl)bis(2-
methylindenyl)stannyl]bis{[bis(diethylamido)]zirconium},
[tetrakis(2-methyl-4phenylindenyl)stannyl]bis{[bis
(diethylamido)]zirconium; [tetrakis(2-methyl-4,5-
benzoindenyl)stannyl]bis{[bis(diethylamido)]zirconium],
[tetrakis(cyclopentadienyl)stannyl]bis{[bis(diethylamido)]
hafnium}, [bis(cyclopentadienyl)bis(indenyl)stannyl]bis{
[bis(diethylamido)]hafnium}, [bis(cyclopentadienyl)bis
(fluorenyl)stannyl]bis{[bis(diethylamido)]hafnium},
[tetrakis(indenyl)stannyl]bis{[bis(diethylamido)]hafnium},
[tetrakis(2-methylindenyl)stannyl]bis{[bis(diethylamido)]
hafnium}, [bis(indenyl)bis(2-methylindenyl)stannyl]bis{
[bis(diethylamido)]hafnium}, [tetrakis(2-methyl-4-
phenylindenyl)stannyl]bis{[bis(diethylamido)]hafnium},
and [tetrakis(2-methyl-4,5-benzoindenyl)stannyl]bis{[bis
(diethylamido)]hafnium}.

9. A process for preparing a polyolefin by polymerization of at least one olefin in the presence of a catalyst, wherein the catalyst comprises at least one organometallic compound of the formula

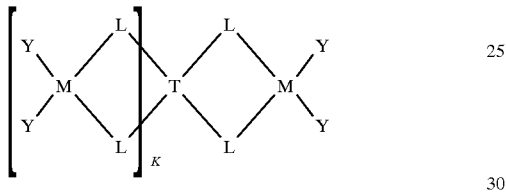

where M are identical or different and are titanium, zirconium, hafnium, vanadium, niobium, tantalum, scandium, yttrium or a rare earth metal, L are, independently of one another, identical or different π ligands or other electron donors, T is a tin-containing bridge, Y are identical or different and are each a $C_1$–$C_{20}$-hydrocarbon group, an amide group, an alkoxy group or a halogen atom and K=1, and at least one cocatalyst.

10. The process as claimed in claim 9, wherein M is titanium, zirconium, hafnium, vanadium, niobium or a rare earth metal.

11. The process as claimed in claim 10 wherein M is titanium, zirconium or hafnium.

12. The process as claimed in claim 11, wherein said cocatalyst is an aluminum or boron compound.

13. The process as claimed in claim 12, wherein said aluminum compound is an aluminumoxane or an aluminum alkyl or a mixture thereof and said boron compound is of the formula $R^3_x NH_{4-x} BR^4_4$, $R^3_x PH_{4-x} BR^4_4$, $R_3 CBR^4_4$ or $BR_3$, where x is a number from 1 to 4, the radicals $R^3$ are identical or different, and are $C_1$–$C_{10}$-alkyl or $C_6$–$C_{18}$-aryl, or two radicals $R^3$ together with the atoms connecting them form a ring, and the radicals $R^4$ are identical or different, and are $C_6$–$C_{18}$-aryl which can be substituted by alkyl, haloalkyl or fluorine.

14. A process for preparing an organometallic compound of the

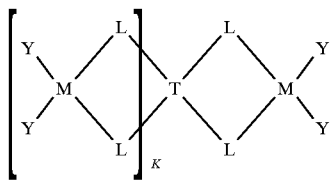

where M are identical or different and are titanium, zirconium, hafnium, vanadium, niobium, tantalum, scandium, yttrium or a rare earth metal,, L are, independently of one another, identical or different π ligands or other electron donors, T is a tin-containing bridge, Y are identical or different and are each an $NR^2_2$ group, where $R^2$ are identical or different an are each hydrogen or a $C_1$–$C_{20}$-hydrocarbon radical, and K=0 or 1, which comprises reacting a compound of the formula II, where L are identical or different and are each a π ligand or another electron donor, T is a bridge and K is zero or 1, with a compound of the formula III, where M are identical or different and are titanium, zirconium, hafnium, vanadium, niobium, tantalum, scandium, yttrium or a rare earth metal, and $R^2$ are identical or different and are each hydrogen or a $C_1$–$C_{20}$-hydrocarbon radical

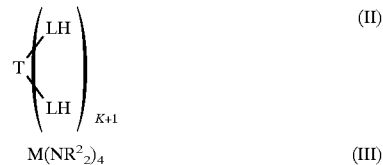

* * * * *